(12) United States Patent
Li et al.

(10) Patent No.: US 11,150,231 B2
(45) Date of Patent: Oct. 19, 2021

(54) METHOD FOR MEASURING A MUDFLAT ELEVATION BY REMOTELY SENSED WATER CONTENT

(71) Applicant: HOHAI UNIVERSITY, Nanjing (CN)

(72) Inventors: Huan Li, Nanjing (CN); Xiaoyan Zhang, Nanjing (CN); Zhiyuan Li, Nanjing (CN); Zijie Yang, Nanjing (CN)

(73) Assignee: HOHAI UNIVERSITY, Nanjing (CN)

( * ) Notice: Subject to any disclaimer, the term of this patent is extended or adjusted under 35 U.S.C. 154(b) by 276 days.

(21) Appl. No.: 16/153,820

(22) Filed: Oct. 7, 2018

(65) Prior Publication Data

US 2019/0041377 A1   Feb. 7, 2019

Related U.S. Application Data

(63) Continuation of application No. PCT/CN2017/115572, filed on Dec. 12, 2017.

(30) Foreign Application Priority Data

Feb. 22, 2017 (CN) .......................... 201710096019.4

(51) Int. Cl.
*G01N 33/24* (2006.01)
*G06F 17/18* (2006.01)
(Continued)

(52) U.S. Cl.
CPC ............. *G01N 33/246* (2013.01); *G01C 5/00* (2013.01); *G01N 21/31* (2013.01); *G06F 17/18* (2013.01); *G06N 7/00* (2013.01)

(58) Field of Classification Search
None
See application file for complete search history.

(56) References Cited

U.S. PATENT DOCUMENTS 9,453,795 B1   9/2016   Loew et al.

FOREIGN PATENT DOCUMENTS

CN    102288954 A    12/2011
CN    103196862 A     7/2013
(Continued)

OTHER PUBLICATIONS

Li et al. "Predicting Water Content Using Linear Spectral Mixture Model on Soil Spectra," J. Appl. Remote Sens., 073539, (2013) (Year: 2013).*

(Continued)

*Primary Examiner* — Roy Y Yi

(57) ABSTRACT

The present disclosure discloses a method for measuring a mudflat elevation based on remotely sensed water content, comprising steps of: measuring a spectral value of a soil surface in a mudflat area using a full-band spectrometer, analyzing a relationship between the spectral value and a soil water content of the mudflat area; building a remotely sensed water content retrieval model using a statistical correlation method; selecting a water sensitive waveband in the remote sensing data, and retrieving the soil water content of the mudflat area; analyzing a relationship between the soil water content and the mudflat likewise using the statistical correlation method; building a relational model between the mudflat water content and an elevation, and applying the model to a satellite image to obtain the mudflat elevation.

4 Claims, 4 Drawing Sheets

(51) Int. Cl.
*G01N 21/31* (2006.01)
*G06N 7/00* (2006.01)
*G01C 5/00* (2006.01)

(56) References Cited

FOREIGN PATENT DOCUMENTS

| CN | 103791890 A | 5/2014 |
| CN | 106767687 A | 5/2017 |

OTHER PUBLICATIONS

Onojeghuo et al. Chracterising Reedbed Using LiDAR Data: Potential and Limitations, IEEE J. Selected Topics in Applied Earth Observations and Remote Sensing, vol. 6, No. 2, 2013, p. 935-941 (Year: 2013).*
Wang et al. (Retrieval and Mapping of Soil Texture Based on Land Surface Diurnal Temperature Range Data from MODIS, PLOS One p. 1-15, 2015 (Year: 2015).*
Justice et al. "The Moderate Resolution Imaging Spectroradiometer (MODIS): Land Remote Sensing for Global Change Research". IEEE Transactions on Geoscience and Remote Sensing vol. 36, No. Jul. 4, 1998, p. 1228-1249 (Year: 1998).*
Lee et al. (Radar Backscattering of Interdial Mudflats observed by Radarsat-1 SAR images and Ground Based Scatterometer Experiments, IEEE Transactions on Geo. and Remote Sensing, vol. 49, No. 5, May 2011 p. 1701-1711). (Year: 2011).*
Internation Search Report of PCT/CN2017/115572, dated Feb. 26, 2018.

\* cited by examiner

METHOD FOR MEASURING A MUDFLAT ELEVATION BY REMOTELY SENSED WATER CONTENT

CROSS-REFERENCE TO RELATED APPLICATIONS

This application is a continuation of International Patent Application No. PCT/CN2017/115572 with a filing date of Dec. 12, 2017, designating the United States, now pending, and further claims priority to Chinese Patent Application No. 201710096019.4 with a filing date of Feb. 22, 2017. The content of the aforementioned applications, including any intervening amendments thereto, are incorporated herein by reference.

FIELD

Embodiments of the present disclosure generally relate to a method for measuring an elevation, and more particularly relate to a method for measuring a mudflat elevation based on remotely sensed water content.

BACKGROUND

Mudflats in China are widely distributed in coastal areas in Liaoning, Shandong, Jiangsu, Zhejiang, Fujian, Taiwan, Guangdong, Guangxi, and Hainan, with a total area of 2.1704 million hectares, approximately three times as large as the land area of the Singapore. Mudflats have huge exploitation potentials, reclamation of which by enclosure may form massive land reservation resources to provide a vast development space in coastal areas for ports, fairways, coastal power plant construction, agricultural production, etc. The intensification of human activities has affected the topography, hydrodynamic patterns, and ecological environments in coastal zones to various extents; therefore, it is needed to timely understand the natural ecological environment changes in the coastal zones through scientific research methodologies such as erosion-deposition evolution analysis, numerical simulation, and ecological environment simulation, etc. However, as important basic data for scientific researches in formulating development plan of coastal zone resources, evaluating and demonstrating environmental impacts, and demonstrating sea area utilizations, mudflat elevations can hardly be obtained.

Currently, the technical methodologies for obtaining a coastal zone elevation based on remote sensing include the Lidar (Light Detection and Ranging) method and the water-line method. Their respective characteristics are provided below:

(1) the Lidar method has extremely high survey expenses; besides, the landform and topography of mudflat areas change very fast and need to be constantly updated; it is apparent that the expenses of using Lidar are hardly affordable for users. Moreover, due to its short development history, a historical database can hardly be formed; without data accumulation, the requirements in dynamic evolution analysis can hardly be satisfied;

(2) Water-line method: Collins and Madge innovatively proposed the "water-line method" for monitoring a mudflat elevation by remote sensing. The water-line method had not made any progress since its introduction till 1995 when Koopmans, a Dutch scholar, applied it to obtain the beach elevation of Wadden Sea area in Europe, and then it aroused the attention of Mason from the University of Reading in England. Mason's researches gradually made the water-line method known to the world. Niedermeier, Heygster, Kim, and Ryu successively obtained mudflat elevations using different sources of remote sensing data, Ryu even believed that the water-line method was the only remote sensing method for monitoring the elevation of a mucky mudflat. Studies on the water-line method in China started in 2003 when HAN Zhen, YUN Caixing, et al determined the changes of lines of the mucky mudflats in Wenzhou area based on MSS, TM, ETM, and SPOT data sources to calculate the gradients and the deposition and erosion rate Later, ZHENG Zongsheng, ZHOU yunxuan et al simulated, tidal levels at the satellite passing time using a hydrodynamic model constructed by a commercial software, Delft3D based on the non-horizontal characteristics of the water lines and assigned values to the water lines extracted from multi-view images, thereby generating the elevation of the Eastern Beach of Chongming Island at the Yangtze Estuary. Afterwards, scholars such as HAN Zhen and ZHAO Bin also made useful attempts on different regions of the Yangtze Estuary. Since 2010, LIU Yongxue, LI Manchun, et al. have applied the water-line method to mudflat areas in Jiangsu and attempted to fuse the MODIS's high temporal resolution characteristic into an image with a relatively high spatial resolution such as TM, which solved the drawback of too large time span in image selection for the water-line method. In 2013, TANG Yuanbin et al extracted the water lines and obtained the elevations of the mudflats of Zhejiang based on the UAV (Unmanned Aerial Vehicle) aerial photography technology. It is seen that the water-line method has been extensively studied around the world; however, this method still has its limitations. Firstly, the water-line method needs assistance with continuous tidal level data, but for those mudflats distant from the coasts, no long-term tide gauge stations are available. Secondly, the water line method presumes that the mudflat elevation at different periods is constant so as to facilitate selecting of water lines at different time phases; however, it is not the case that the mudflat elevation does not change; instead, the mudflat elevation will change dramatically within a short time in certain areas, which will affect the accuracy of obtaining the elevation by the water line method. Therefore, errors will be relatively large when applying, the water line method to measure the mudflat elevation in a fast-changing area.

SUMMARY

An object of the present disclosure is to provide a measurement method of retrieving mudflat soil surface water content based on a remotely sensed image to thereby indirectly obtain a mudflat elevation. After ebbing, the mudflat is gradually exposed, where an area with a high terrain is exposed earlier with a low water content, while an area with a low terrain is exposed later with a high water content; therefore, the water content of the exposed mudflat surface is inversely correlated with the elevation, such that as long as an appropriate remotely sensed image is selected, the mudflat elevation may be indirectly measured by retrieving the surface soil water content of the mudflat.

To solve the technical problem above, the present disclosure adopts a technical solution below:

The present disclosure provides a method for measuring a mudflat elevation based on remotely sensed water content, comprising steps of:

(1) collecting soil samples: selecting a mudflat area as a to-be-measured area, selecting a plurality of collection sites in the to-be-measured area, collecting soil samples at respective collection sites, and measuring surface spectral data of the respective soil sample;

(2) measuring water content: synchronously measuring the water content of respective soil samples in the step (1), i.e., a percentage of water mass over soil mass in the soil samples;

(3) building a water content retrieval model based on the spectral data: analyzing, by statistical regression, the surface spectral data derived from the step (1) and the water content data derived from the step (2), and building a spectrum-water content relational model;

(4) applying the water content retrieval model derived from the step (3) to a remotely sensed image, and obtaining a spatial distribution map of mudflat surface water content based on remote sensing spectral data;

(5) extracting water content values of the collection sites in the step (1) from the spatial distribution map of mudflat surface water content obtained in the step (4), measuring elevation data of respective collection sites, regressively analyzing the elevations and water content values of respective collection sites, and building a water content-elevation relational model;

(6) building a mudflat elevation inversion model based on the "spectrum-water content" model in the step (3) and the "water content-elevation" model in the step (5) with the water content as a common variable for model coupling;

(7) inputting the spectral data of the remotely sensed image of the to-be-measured area into the inversion model of the step (6) to thereby perform remote sensing measurement of the mudflat elevation.

As a further preferred embodiment of the solution of the present disclosure, at least 30 collection sites are selected in the step (1).

As a further preferred embodiment of the solution of the present disclosure, the soil samples are subjected to spectrum measurement using a ground-object spectroradiometer.

As a further preferred embodiment of the solution of the present disclosure, a method of measuring the water content in the step (2) comprises: immediately drying the soil sample that just underwent the spectrum measurement at 150° C. till the mass has no change, and calculating a percentage of water mass evaporated by drying over the dried soil mass to obtain the water content of the soil sample.

As a further preferred embodiment of the solution of the present disclosure, the regression analysis process is performed using the SPSS software.

An advantageous effect of the present disclosure lies in that: with the remotely sensed water content as a bridge to connect the spectrum and the elevation, the present disclosure provides a physical medium between the objects that were originally not linkable, which simplifies the process of mudflat elevation measurement; the remote sensing satellite data used in the present disclosure may be freely downloaded, such that only with a satellite image map, the mudflat elevation may be measured by remote sensing of the water content according to the present disclosure, which significantly reduces the cost of mudflat elevation measurement; besides, the measurement accuracy of the present disclosure is higher than the water-line method and the Lidar technology in the prior art.

DETAILED DESCRIPTION OF EMBODIMENTS

Figure 1:
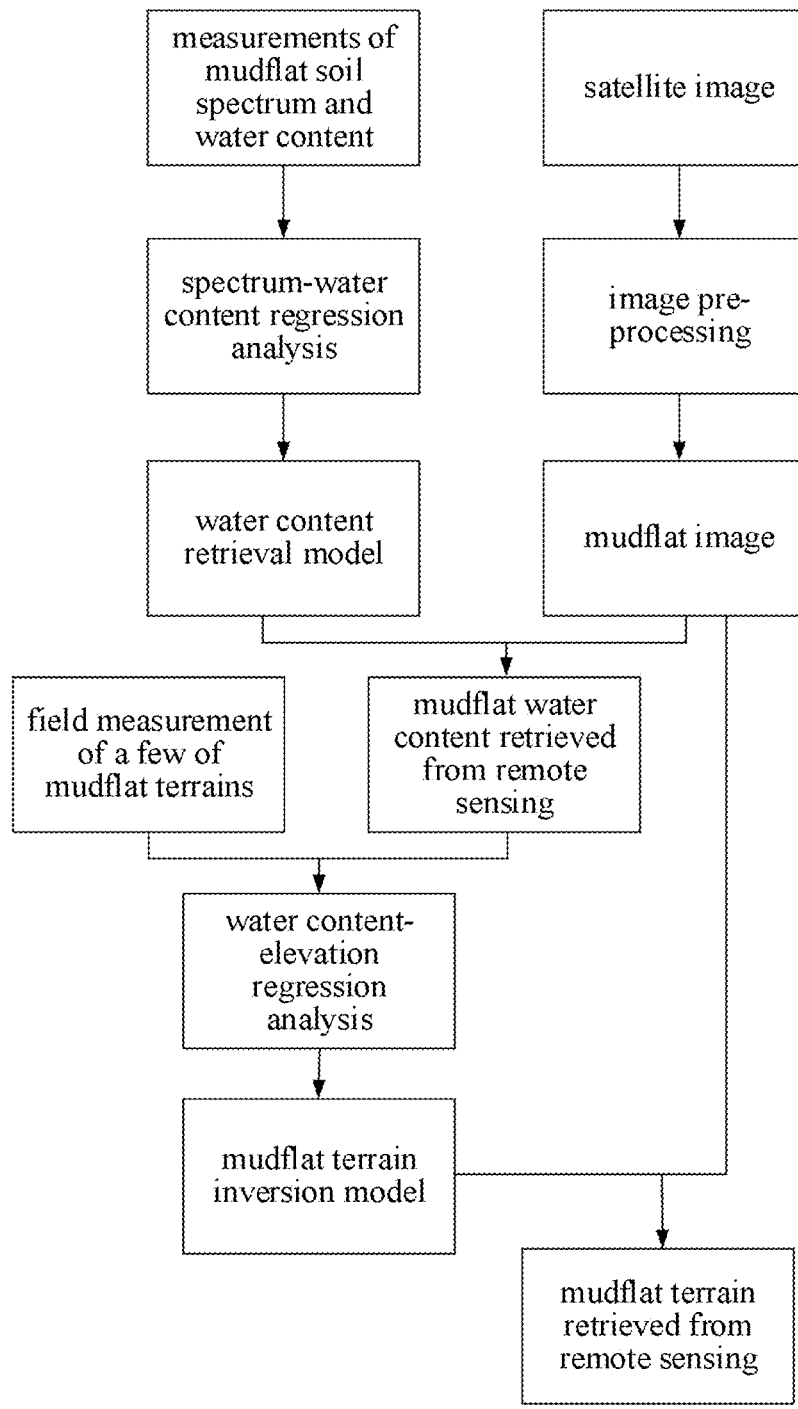
FIG. 1 is the technical line map of the present disclosure.

To make the implementation technical means, the innovative features, and the objects to be achieved of the present disclosure apparent and easily understood, the present disclosure will be further illustrated with reference to the preferred embodiments.

With a certain mudflat in Jiangsu Province as an example, a bear mudflat is selected; the present disclosure builds an inversion model of a mudflat elevation based on field survey, measurement, sampling, and indoor sample analysis, to realize a low-cost fast acquisition of the mudflat elevation. A process of implementing the present disclosure is provided below:

(1) Building a Water Content Retrieval Model

Spectral data: in the to-be-measured area, measuring, surface spectral data of the bare mudflat using a spectroradiometer where 30 collection sites or above are selected;

Water content data: synchronous with the spectrum measurement above, taking the soil samples, which just underwent spectrum measurement in standard small aluminum cases (9 cm in diameter, 3 cm in height) specified to use in the pedology field, back to the laboratory, drying them to measure the water content of respective sites; the process of measuring the water content includes: drying the soil sample at 105° C. for 12 hours to ensure its mass constant; taking it out into a dryer for use; calculating the percentage of the soil sample lost mass (i.e., water mass evaporated due to drying) over the mass of the dried soil, thereby obtaining the mass water content θ of the soil;

Inversion Model: analyzing the relationship between the spectrum and the water content by statistic regression using the SPSS software, and building a spectrum-water content relational model. The Landsat TM/ETM+/OLI data at the TM7 waveband are most appropriate for retrieving the mudflat soil water content. Because the central wavelength at the TM7 waveband is 2220 nm, the water content retrieval model is built with the spectral reflectivity $R_{2220}$ at this waveband as the independent variable and the soil water content θ as the dependent variable, $\theta = -106.27 \times R_{2220} + 39.197$.

(2) applying the water content retrieval model to a satellite image to invert the mudflat water content:

Remote sensing data: the remote sensing data may be downloaded freely from www.usgs.gov; the available data include satellite images obtained by three sensors: Landsat TM, ETM+, and OLI.

Pre-processing of the remote sensing data: remote sensing data and processing belong to conventional means, including: atmospheric correction using the FLAASH module in the ENVI remote-sensing processing software, geological correction using the Registration module, and extracting a mudflat area from the satellite image using the Supervised classification module; after processing through the steps above, obtaining a spectral reflectivity image of the mudflat area; selecting the spectral reflectivity image with the central wavelength of 2220 nm for use to obtain a spectral reflectivity that may be entered in the inversion model.

Water Content Inversion: applying, with the Band Math module in the ENVI remote-sensing processing software, the water content retrieval model to the mudflat spectral reflectivity image with the central wavelength of 2220 nm, obtaining a water content value of each pixel in the mudflat image, and further obtaining a spatial distribution map of water content of the mudflat area.

(3) Building a Water Content—Elevation Regression Model

Field Measured Elevation Data: measuring a few discrete sites in the mudflat area using RTK-GPS; generally, 30 measurement sites need to be evenly distributed in the to-be-measured area.

Water Content-Elevation Regression Analysis: extracting the water content values of the 30 measurement sites from the spatial distribution map of water content, statistically analyzing the relationships between the elevation values and the water contents of the measurement sites, and building a water content-elevation relational model.

With the mudflat as an example, the elevation-water content relational model is $H=-0.16\theta^2+0.8766\times\theta-11.159$, where H denotes the elevation, and $\theta$ denotes the water content.

(4) Building an Elevation Inversion Model to Be Applied to Invert the Elevation from the Mudflat Image A spectrum-elevation mathematical model may be derived with the water content $\theta$ as a bridge based on the mudflat water content model retrieved from remote sensing and the mudflat soil water content-elevation statistical model, thereby building a mudflat elevation inversion model $H=-180.693\times(R_{2220})^2+40.139\times R_{2220}-1.381$;

inputting, with a module in the ENVI remote-sensing processing software, the elevation inversion model to be applied to the mudflat spectral reflectivity image with the central wavelength of 2220 nm, to obtain an elevation value of each pixel in the mudflat image, thereby realizing a rapid remote sensing of the mudflat elevation.

Figure 2:
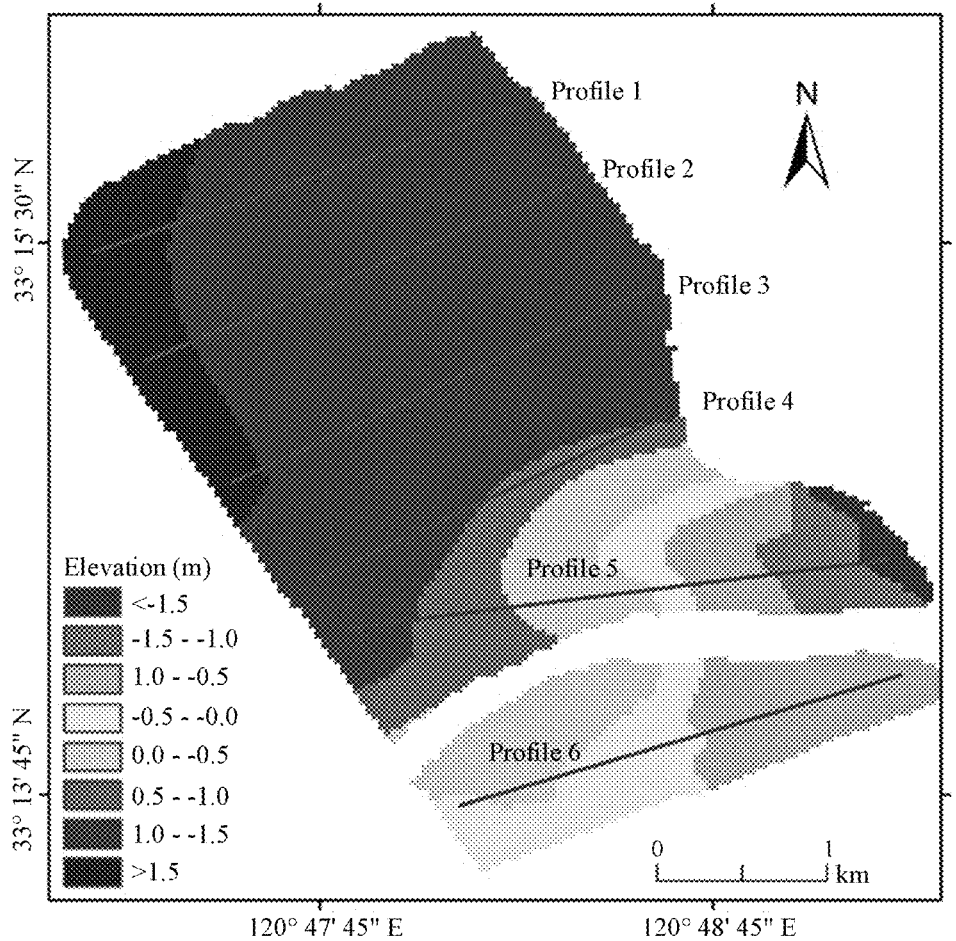
FIG. 2 is a position distribution map of verified profiles in the obtained mudflat elevation inversion model according to an embodiment of the present disclosure.
Figure 3:
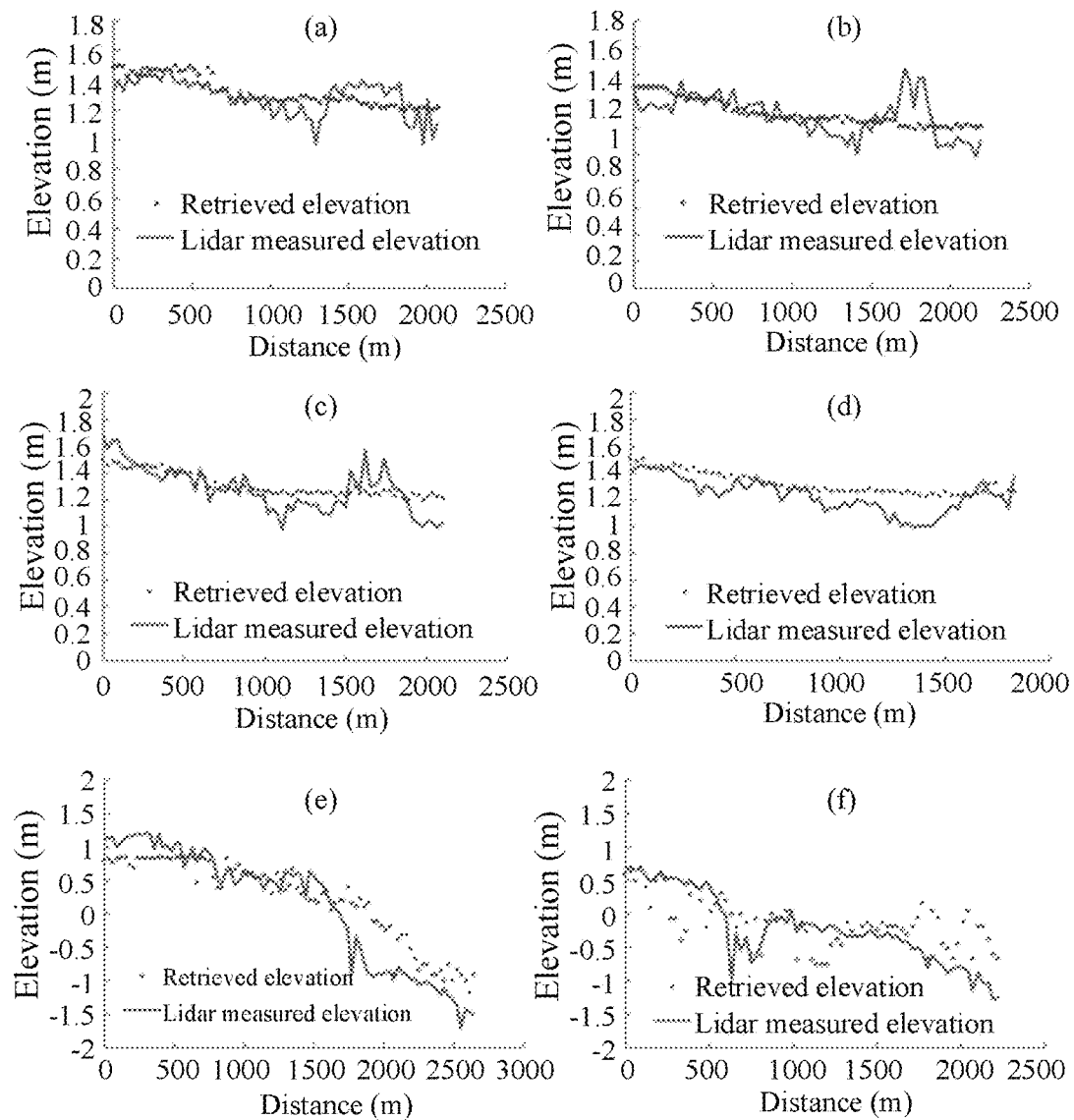
FIG. 3 is a comparison diagram between elevations of respective profiles in the mudflat elevation inversion model in FIG. 2 and in situ measured elevations.

The elevation inversion model obtained from the method above is verified in a process provided below:

as shown in FIG. 2, taking 6 profiles from the in situ measured elevation map and the inversion elevation map, respectively, and obtaining a comparison diagram between the elevations of the respective profile positions in the actual measurement model and the inversion model, as shown in FIG. 3, it may be seen from the diagram that the retrieved elevations approach to a substantial consistency with the in situ measured elevations, and the model has a good inversion effect.

TABLE 1

Check the Accuracy of Remote-Sensing Retrieved Elevations

| | Mean Absolute Error MAE (cm) | Mean Relative Error ARE (%) |
|---|---|---|
| Profile 1 | 8.2 | 7 |
| Profile 2 | 10.0 | 8 |
| Profile 3 | 9.4 | 8 |
| Profile 4 | 9.1 | 8 |
| Profile 5 | 26.3 | 33 |
| Profile 6 | 30.2 | 45 |
| Overall | 19.2 | 24 |

By evaluating the inversion results using the average absolute values and the average relative errors, it may be seen from Table 1 that:

(1) Profile 1~Profile 4 are flat terrain areas. It may be seen that the inversion accuracy is controlled at a very high level, and the mean absolute errors MAE of the elevations measured by remote sensing are all smaller than 10 cm, and the relative errors are also very low, only about 8%, which indicates that the elevation inversion accuracy is as high as 92%;

(2) Profile 5~Profile 6 are areas with a relatively large undulation; the inversion accuracy is slightly lower, and the error is slightly larger than the flat area; but they are still controlled at a 30 cm accuracy level.

Figure 4:
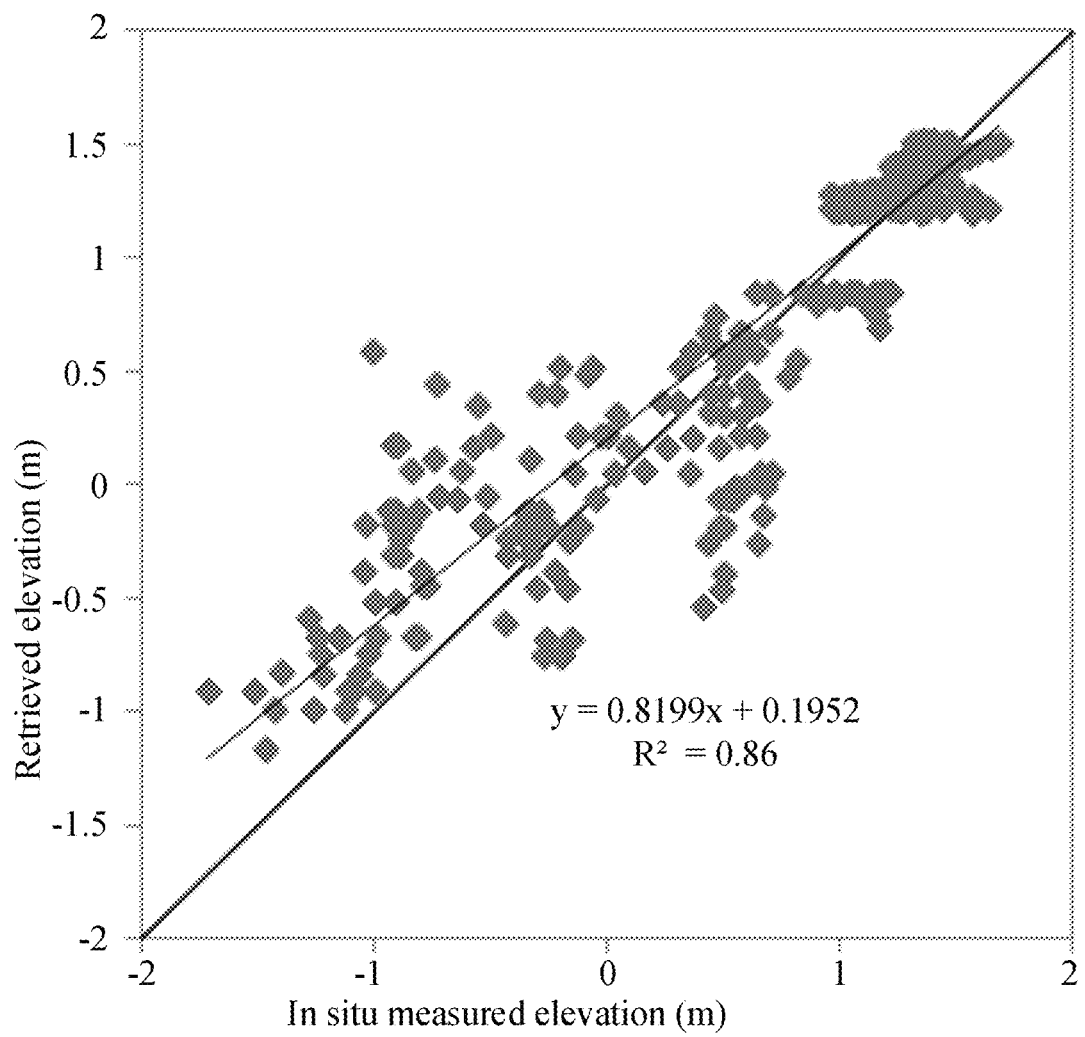
FIG. 4 is a scatter plot for the elevations of respective profiles in the mudflat elevation inversion model and in situ measured elevations in an embodiment of the present disclosure.

(3) the overall accuracy analysis: the errors of the elevations obtained by means of remotely sensed water content are controlled within 20 cm, which is apparently superior to the accuracy level of Lidar measurement What has been described above relates to verifying the inversion accuracy by profile comparison, and there is another method that may also verify the inversion accuracy. That is, calculating a multiple correlation coefficient by drawing a scatter plot of retrieved elevation values and the in situ measured elevation values, and using a multiple correlation coefficient to evaluate the inversion accuracy. As shown in FIG. 4, the scattered dots are basically distributed near the diagonal line; moreover, the scattered dots have a relatively high fitting degree, and the multiple correlation coefficient reaches 0.86.

The verification results indicate that the mudflat elevation retrieved from the remotely sensed water content has a relatively high accuracy, which may satisfy the needs in dynamically analysis of coastal zone topography.

Those of normal skill in the art should understand that the embodiments above are only for illustrating the present disclosure, not for limiting; all variations and transformations of the embodiments within the substantive spirit of the present disclosure should fall within the protection scope of the claims of the present disclosure.

We claim:

1. A method for measuring a mudflat elevation based on remotely sensed water content, comprising steps of:
    (1) collecting soil samples: selecting a bare mudflat area as a to-be-measured area, selecting a plurality of collection sites in the to-be-measured area, collecting soil samples at respective collection sites, and measuring surface spectral data of the soil samples;
    (2) measuring water content: synchronously measuring the water content of respective soil samples in the step (1), the water content referring to a percentage of water mass over soil mass in the respective soil sample;
    (3) building a water content retrieval model based on the spectral data: analyzing, by statistical regression, the surface spectral data derived from the step (1) and the water content data derived from the step (2), and building a spectrum-water content relational model;
    (4) applying the water content retrieval model derived from the step (3) to a remotely sensed image, and obtaining a spatial distribution map of mudflat surface water content based on remote sensing spectral data;
    (5) extracting water content values of the collection sites in the step (1) from the spatial distribution map of mudflat surface water content obtained in the step (4), measuring elevation data of respective collection sites, regressively analyzing the elevations and water content values of respective collection sites, and building a water content- elevation relational model;

(6) building a mudflat elevation inversion model based on the "spectrum - water content" model in the step (3) and the "water content-elevation" model in the step (5) with the water content as a common variable for model coupling;

(7) inputting the spectral data of the remotely sensed image of the to-be-measured area into the inversion model of the step (6) to thereby perform remote sensing measurement of the mudflat elevation.

2. The method for measuring a mudflat elevation based on remotely sensed water content according to claim 1, wherein at least 30 collection sites are selected in the step (1).

3. The method for measuring a mudflat elevation based on remotely sensed water content according to claim 1, wherein the soil samples are subjected to spectrum measurement using a ground-object spectroradiometer.

4. The method for measuring a mudflat elevation based on remotely sensed water content according to claim 1, wherein a method of measuring the water content in the step (2) comprises: immediately drying the soil sample that just underwent the spectrum measurement at 150° C. till the mass has no change, and calculating a percentage of water mass evaporated by drying over the dried soil mass to obtain the water content of the soil sample.

\* \* \* \* \*